United States Patent
Alsumaiti et al.

(10) Patent No.: US 11,913,865 B2
(45) Date of Patent: Feb. 27, 2024

(54) IN-SITU PREDICTION AND DYNAMIC VISUALIZATION OF RELATIVE PERMEABILITY AND CAPILLARY PRESSURE IN POROUS MEDIUM

(71) Applicant: Khalifa University of Science and Technology, Abu Dhabi (AE)

(72) Inventors: Ali M. Alsumaiti, Abu Dhabi (AE); Abdul Ravoof Shaik, Abu Dhabi (AE); Waleed Alameri, Abu Dhabi (AE); Saikrishna Kanukollu, Abu Dhabi (AE)

(73) Assignee: KHALIFA UNIVERSITY OF SCIENCE AND TECHNOLOGY, Abu Dhabi (AE)

( * ) Notice: Subject to any disclaimer, the term of this patent is extended or adjusted under 35 U.S.C. 154(b) by 848 days.

(21) Appl. No.: 16/737,520

(22) Filed: Jan. 8, 2020

(65) Prior Publication Data
US 2021/0208050 A1  Jul. 8, 2021

(51) Int. Cl.
*G01N 15/08* (2006.01)
*G01N 33/24* (2006.01)
*G06F 30/27* (2020.01)
*G06N 20/00* (2019.01)
*G06N 5/04* (2023.01)

(52) U.S. Cl.
CPC .......... *G01N 15/082* (2013.01); *G01N 33/24* (2013.01); *G06F 30/27* (2020.01); *G06N 5/04* (2013.01); *G06N 20/00* (2019.01)

(58) Field of Classification Search
CPC .............................. G06N 20/00; G01N 15/082
(Continued)

(56) References Cited

U.S. PATENT DOCUMENTS

2019/0056376 A1* 2/2019 Youssef ............... G01N 15/082
2020/0041692 A1* 2/2020 Schmedes ............... E21B 49/00
(Continued)

OTHER PUBLICATIONS

Zhao et al. "A Hybrid Approach for the Prediction of Relative Permeability Using Machine Learning of Experimental and Numerical SCAL Data" Oct. 2, 2019, SPE, pp. 1-24. (Year: 2019).*
(Continued)

*Primary Examiner* — Ricky Go
(74) *Attorney, Agent, or Firm* — MH2 TECHNOLOGY LAW GROUP, LLP

(57) ABSTRACT

There is provided a method and apparatus for accelerated in-situ prediction and dynamic visualization of characteristics of a porous medium, including an input source for inputting data from computer-aided simulations and real-time core flooding experiments, an embedded hardware unit comprising of a processor running a prediction model with inferences of porous medium samples, and a human-machine interface comprising a display unit for displaying the estimated plurality of characteristics of the porous medium and an input unit for accepting commands from a user. The input source is in real-time communication with the embedded hardware unit and the display unit and the apparatus reduces a total analysis time taken for characterizing the porous medium. Further, the porous medium is a rock sample and the plurality of properties of the porous medium comprises the relative permeability ($K_r$) and capillary pressure ($P_c$) characteristics of the porous medium.

13 Claims, 1 Drawing Sheet

(58) Field of Classification Search
USPC .......................................................... 702/2
See application file for complete search history.

(56) References Cited

U.S. PATENT DOCUMENTS

| | | | | |
|---|---|---|---|---|
| 2020/0401951 | A1* | 12/2020 | Ranganathan | G01V 1/306 |
| 2021/0010351 | A1* | 1/2021 | Sun | G06N 20/00 |
| 2021/0041596 | A1* | 2/2021 | Kushwaha | G01V 1/282 |
| 2021/0042634 | A1* | 2/2021 | Maucec | G06F 16/906 |
| 2021/0062638 | A1* | 3/2021 | Crouse | G01V 99/005 |

OTHER PUBLICATIONS

Williams et al. "Accurate Estimates of in-situ Porosity and Permeability Data Using Cloned Parametric Stressed Models—A Hybrid Approach" Sep. 22, 2010, SPE, pp. 1-11. (Year: 2010).*

Zhao et al. "Permeability Prediction in a Heterogeneous Reservoir Using Soft Computing Technologies" Apr. 27, 2018; SPE, pp. 1-19. (Year: 2018).*

Shaik et al. "Rock Classification Based on Micro-CT Images using Machine Learning Techniques" Nov. 14, 2019, SPE, pp. 1-11. (Year: 2019).*

Al-Fattah et al. "Artificial-Intelligence Technology Predicts Relative Permeability of Giant Carbonate Reservoirs" Sep. 7, 2007, SPE, pp. 1-8. (Year: 2007).*

Zhao et al., "A Hybrid Approach for the Prediction of Relative Permeability Using Machine Learning of Experimental and Numerical SCAL Data," Oct. 2019, SPE International, SPE-196022-MS, pp. 1-24. (Year: 2019).*

Moreira et al., "Application of MCMC Optimization Method to Estimate Relative Permeability of Carbonate Rocks from Unsteady-State Core Flood Experiments," Jun. 2019, SPE International, SPE-195562-MS, pp. 1-12. (Year : 2019).*

* cited by examiner

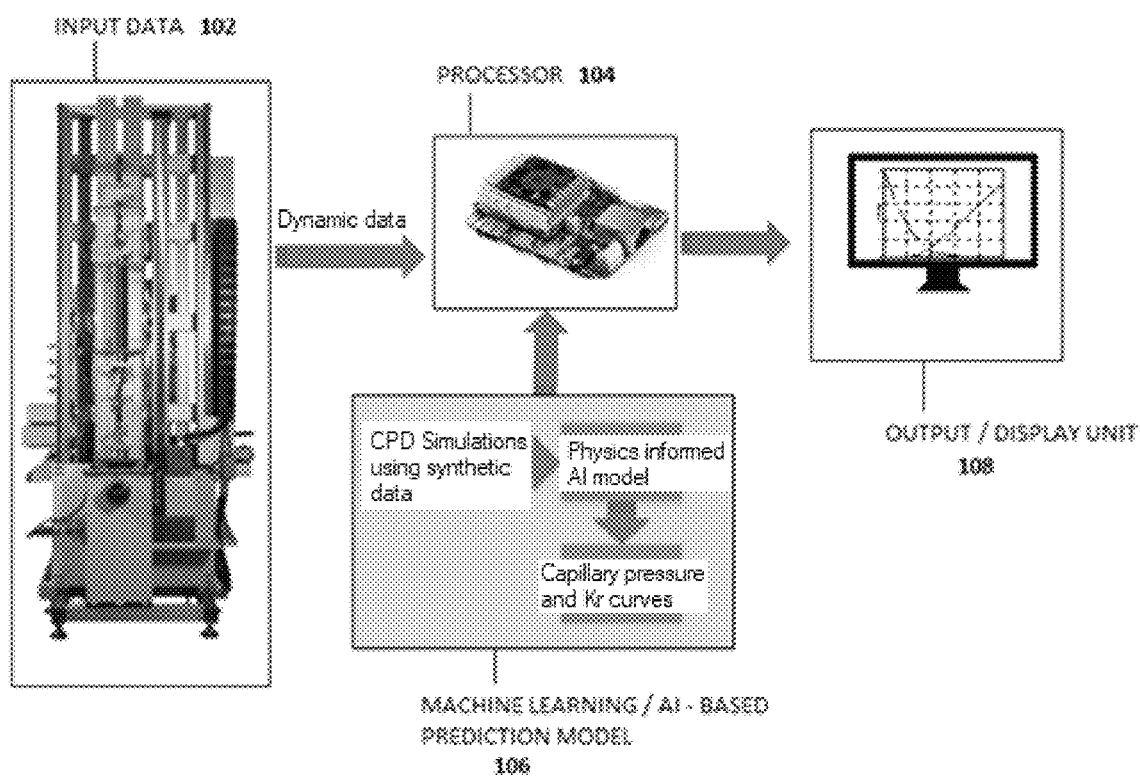

IN-SITU PREDICTION AND DYNAMIC VISUALIZATION OF RELATIVE PERMEABILITY AND CAPILLARY PRESSURE IN POROUS MEDIUM

FIELD OF THE INVENTION

The present invention relates to the field of core flooding systems, and more particularly to a system and method for facilitating accelerated in-situ core flooding analysis of porous rock samples.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Porous medium systems are complex and so are the processes that determine the movement of two (or more) immiscible phases within their porous structure; nevertheless, special core analysis (SCAL) data provides the foundation for the theory of multiphase flow in porous media. SCAL data such as capillary pressure and relative permeability curves are traditionally obtained from post processing analysis of experimental measurements. As a matter of fact, the petroleum literature provides many examples for water/oil, system on a variety of rocks and that have in turn allowed for the identification of useful trends regarding the general character of these functions; while the shape of the capillary pressure function can be directly related to the pore size distribution of a given rock. The landmarks of a relative permeability curve (curvature, end-point values) are indicators of the difference in wettability for the two fluids inside the porous medium. Hence, it can be said with confidence that reliable and representative SCAL data is essential to determine oil recovery in petroleum reservoirs. Typically, SCAL data is acquired from core sample tests which are in principle representative of reservoir displacements. To characterize SCAL data, it is necessary to perform measurements of relative fluid flow properties in the porous medium.

Core Flooding is a common test used to determine rock properties and mimic fluid-fluid and rock-fluid interaction in porous medium. Previously analytical and/or simulation tools are used to post process the core flooding data. For example, it is difficult to get correct relative permeability from steady state core flooding experiment because of core heterogeneity, effect of capillarity and gravity forces. It's worth noting that capillary end effect can play an important role when interpreting or designing a core flood experiment. The outlet of the core is characterized by a zero capillary pressure which can trap wetting phase in a region near the outlet of the core, potentially leading to a wrongful estimation of parameters such as residual saturation and relative permeability. In oil and gas industry, it is common practice to construct a core flooding simulation model to reproduce an experimental data. Interpretation results are utilized to generate representative relative permeabilities on the core. This method can deal with all kinds of effects such as capillary and gravity forces. Especially in history-matching process, the result depends on individual engineer's skill and it is time consuming to reach the best match. Furthermore, there is no guarantee to assure that it is the optimum unique solution.

Several analytical/semi analytical models are proposed in literature to interpret capillary pressure and relative permeability from core flooding data. However, most of the analytical models have several limitations including proper characterization of capillary end effect. For this purpose several commercial simulation models are developed and used in the petroleum industry to estimate capillary pressure and relative permeability. Eclipse 100, CMG IMEX, Sendra and Cydarex are some of the tools that are used for this purpose. However, all these models need a physical human interference to perform the analysis.

Accordingly, there exists a need for an accelerated and automated post processing technique for analysis of core flooding data, which overcomes the disadvantages of previously or traditionally deployed techniques.

SUMMARY OF THE INVENTION

Therefore it is an object of the present invention to provide an accelerated and automated post-processing technique for core flooding data.

The present invention involves an in-situ method of estimating a plurality of porous medium properties, the method comprising the steps of obtaining data from real-time core flooding experiments being conducted on a porous medium, sending the obtained data to an embedded hardware unit running a machine learning prediction model, and using the machine learning prediction model along with the obtained data for estimating and displaying the plurality of porous medium properties on a display unit, wherein the in-situ method reduces a total analysis time taken for characterizing the porous medium.

In another embodiment of the present invention, the plurality of properties of the porous medium comprise relative permeability ($K_r$) and capillary pressure ($P_c$) of the porous medium.

In another embodiment of the present invention, the porous medium is a rock sample.

In another embodiment of the present invention, the method is an accelerated post-processing technique for core flooding data.

In another embodiment of the present invention, the obtained data comprises real-time core flooding data from core flooding experiments and computer aided rock simulations.

In another embodiment of the present invention, the embedded hardware unit is an Artificial Intelligence (AI) based real-time processor.

In another embodiment of the present invention, the machine learning prediction model is run as an inference on the embedded hardware and is executed in real-time.

As another aspect of the present invention, an apparatus is disclosed for in-situ estimation and dynamic visualization of a plurality of characteristics of a porous medium, the apparatus comprising an input source for inputting data from computer-aided simulations and real-time core flooding experiments, an embedded hardware unit comprising of a processor running a prediction model with inferences of porous medium samples, and a human-machine interface comprising a display unit for displaying the estimated plurality of characteristics of the porous medium and an input unit for accepting commands from a user, wherein the input source is in real-time communication with the embedded hardware unit and the display unit and the apparatus reduces a total analysis time taken for characterizing the porous medium.

In another embodiment of the present invention, the plurality of characteristics of the porous medium comprise relative permeability ($K_r$) and capillary pressure ($P_c$) of the porous medium.

In another embodiment of the present invention, the porous medium is a rock sample.

In another embodiment of the present invention, the estimation of the plurality of characteristics of the porous medium is based on a Machine Learning (ML) inferences trained based on real-time offline simulations running on the embedded hardware unit.

In another embodiment of the present invention, the user views results of the real-time core flooding experiments on the display unit and is capable of subsequently modifying experimental protocol.

In another embodiment of the present invention, the prediction model is run on an Artificial Intelligence (AI) based real-time processor.

In another embodiment of the present invention, the prediction model is run on a Machine Learning (ML) based real-time processor.

In another embodiment of the present invention, the apparatus is used for implementing an accelerated post-processing technique for core flooding data.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which—

The FIGURE depicts an overall architecture of the system in accordance with the present invention.

DETAILED DESCRIPTION OF THE INVENTION

The aspects of the method and system to provide an accelerated and dependable post processing technique for core flooding data according to the present invention, will be described in conjunction with the attached FIGURE. In the Detailed Description, reference is made to the accompanying FIGURE, which form a part hereof, and in which is shown by way of illustration specific embodiments in which the invention may be practiced. It is to be understood that other embodiments may be utilized, and logical changes may be made without departing from the scope of the present invention. The following detailed description, therefore, is not to be taken in a limiting sense, and the scope of the present invention is defined by the appended claims.

Currently, in order to characterize special core analysis (SCAL) data, it is necessary to perform measurements of relative fluid flow properties in the porous medium. Core flooding methods employed currently require at least two weeks to obtain this fluid flow characteristic. It is currently necessary to prepare core samples with sufficient pore volume to capture the fluids production at the outlet and characterize the properties of the medium (typically several milliliters). Accordingly, typical sample sizes are of the order of 5 cm in diameter and 10 cm in length. The samples are initially saturated with 100% water before it is drained with oil to connate water saturation and aged at a targeted temperature for at least two weeks. Once the core restores its wettability, the sample is loaded in the core flooding system to perform water flooding.

Wettability is defined as the ability of a liquid to maintain contact with a solid surface and is controlled by the balance between intermolecular interactions of an adhesive type (liquid to surface) and cohesive type (liquid to liquid). In the oil industry, water flooding (or water injection) involves injecting water into an oil field, usually to increase pressure and thereby stimulate production. Both water injection and gas injection methods are used in reservoir management in order to increase oil recovery from an existing reservoir.

The present invention deals with an artificially intelligent method and device that executes this method in an efficient fashion both combined facilitating in-situ core flooding analysis of porous rock samples, and presents an apparatus and method to accelerate the process of characterizing two-phase flow analysis of a rock sample through digital rock inference running on a powerful real-time processor. The invention discloses a method for predictive rock analysis and a hardware unit (or processor) for running machine-learning inferences of rock models. The first part of the invention involves a procedure and method for predictive reservoir simulation modeling using extensive data from computer aided rock simulations and core flooding experiments. The second part of the invention includes an apparatus consisting of an artificially intelligent processor, denoted as processor 104 in the FIGURE, for predicting the in-situ relative permeability ($K_r$) and capillary pressure ($P_c$) characteristics of a rock sample using machine learning inference. The ML inference can either be a pure machine learning model or a hybrid model of machine learning, and a plurality of quantitative models to obtain best accuracy. Typically rock flooding systems are used to investigate interaction between fluid-fluid and rock-fluid interaction. The present invention relates to estimating capillary pressure and relative permeability curve dynamically. The system architecture in accordance with the present invention is depicted in the FIGURE.

Permeability is the property of rocks that is an indication of the ability for fluids (gas or liquid) to flow through rocks. High permeability allows fluids to move rapidly through rocks. Permeability is important for determining an effective reservoir. Porosity and permeability are two properties describing the reservoir rock capacity with regard to fluid continence. Capillary Pressure measurements are made on rock samples for characterizing the fluid filling behavior of a rock sample. This is useful to model an initial hydrocarbon filling event of a reservoir (and hence determine the theoretical hydrocarbon in place) as well as determining the height above free water for each sample which allows a more realistic determination of formation saturation.

In a preferred embodiment of the present invention, as shown in the FIGURE, the proposed apparatus facilitates a real-time communication interface with the core flooding experimental setup (or a core flooding system) as the input source 102 for a Machine Learning or Artificial Intelligence—based prediction model (ML/AI Inference) 106 running at the heart of an embedded hardware or processor 104. This offers real-time processing of rock models based on the input data 102 and subsequently predict $K_r$ and $P_c$ characteristics of the rock model onto a display unit 108 for dynamic visualization of the predicted characteristics. A user views the possible result of the core flooding experiment and subsequently decides to either terminate the experiment or continue with further analysis. For example, this is of great use for accelerating the testing of rock samples for post-analysis of steady state core flooding. The Machine Learning or Artificial Intelligence—based prediction model (ML/AI Inference) 106 includes simulations using synthetic data, a physics informed AI model and relative permeability—capillary pressure curves.

In another embodiment, the proposed system utilizes an embedded hardware designed with an Artificial Intelligence (AI) capable processor 104 for predicting the rock characteristics based on real-time core flooding data acquisition and ML inference of the rock properties. These type of systems have been extensively being used in other applications such as speech synthesis, image recognition and object detection which can be seen in autonomous vehicle navigation systems and mobile phones. While the application of machine learning and artificial intelligence has reached to an advanced level in these areas, this has not been adapted to other fields such as enhanced oil recovery studies. This requires extensive study of rock flooding characteristics and training of machine learning models. This invention addresses this gap by developing a dedicated hardware capable of predicting relative permeability and capillary pressure based on the core flooding experimental data. The hardware is of great use for oil and gas exploration industries by minimizing the time taken for studying the rock samples in the laboratory. The apparatus could drastically cut down the analysis time from days to minutes due to the capabilities of optimally trained digital rock model running on a real-time processor.

Accordingly, in-situ prediction and dynamic visualization of relative permeability and capillary pressure in a porous medium is implemented. The present invention is an inevitable innovation for oil and gas companies, commercial service labs and research entities.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. An in-situ method of estimating a plurality of porous medium properties, the method comprising the steps of:
    obtaining data from real-time core flooding experiments being conducted on a porous medium;
    sending the obtained data to an embedded hardware unit running a machine learning prediction model;
    using the machine learning prediction model along with the obtained data for estimating and displaying the plurality of porous medium properties on a display unit;
    wherein the in-situ method reduces a total analysis time taken for characterizing the porous medium, and accelerates characterizing two-phase flow analysis of the porous medium; and wherein the machine learning prediction model is run as an inference on the embedded hardware and is executed in real-time.

2. The method of claim 1, wherein the plurality of properties of the porous medium comprise relative permeability ($K_r$) and capillary pressure ($P_c$) the porous medium.

3. The method of claim 1, wherein the porous medium is a rock sample.

4. The method of claim 1, wherein the method is an accelerated post-processing technique for core flooding data.

5. The method of claim 1, wherein the obtained data comprises real-time core flooding data from core flooding experiments and computer aided rock simulations.

6. The method of claim 1, wherein the embedded hardware unit is an Artificial Intelligence (AI) based real-time processor.

7. An apparatus for in-situ estimation and dynamic visualization of a plurality of characteristics of a porous medium, the apparatus comprising:
    an input source for inputting data from computer-aided simulations and real-time core flooding experiments;
    an embedded hardware unit comprising of a processor running a prediction model with inferences of porous medium samples, and
    a human-machine interface comprising a display unit for displaying the estimated plurality of characteristics of the porous medium and an input unit for accepting commands from a user;
        wherein the input source is in real-time communication with the embedded hardware unit and the display unit and the apparatus reduces a total analysis time taken for characterizing the porous medium, and accelerates characterizing two-phase flow analysis of the porous medium; and
        wherein the estimated plurality of characteristics of the porous medium is based on a Machine Learning (ML) inferences trained based on real-time offline simulations running on the embedded hardware unit.

8. The apparatus of claim 7, wherein the plurality of characteristics of the porous medium comprise relative permeability ($K_r$) and capillary pressure ($P_c$) the porous medium.

9. The apparatus of claim 7, wherein the porous medium is a rock sample.

10. The apparatus of claim 7, wherein the user views results of the real-time core flooding experiments on the display unit and is capable of subsequently modifying experimental protocol.

11. The apparatus of claim 7, wherein the prediction model is run on an Artificial Intelligence (AI) based real-time processor.

12. The apparatus of claim 7, wherein the prediction model is run on a Machine Learning (ML) based real-time processor.

13. The apparatus of claim 7, wherein the apparatus is used for implementing an accelerated post-processing technique for core flooding data.

* * * * *